United States Patent [19]

Kwak et al.

[11] Patent Number: 4,637,698

[45] Date of Patent: Jan. 20, 1987

[54] PHOTOCHROMIC COMPOUND AND ARTICLES CONTAINING THE SAME

[75] Inventors: Won S. Kwak, Akron; Rodney J. Hurditch, Doylestown, both of Ohio

[73] Assignee: PPG Industries, Inc., Pittsburgh, Pa.

[21] Appl. No.: 635,696

[22] Filed: Jul. 30, 1984

Related U.S. Application Data

[63] Continuation-in-part of Ser. No. 548,600, Nov. 4, 1983, abandoned.

[51] Int. Cl.⁴ .......................... G02B 5/23; G02F 1/01
[52] U.S. Cl. ..................... 351/163; 350/354; 544/71; 252/586; 252/600; 430/345
[58] Field of Search ............... 252/586, 600; 350/354; 430/345; 544/71; 351/163

[56] References Cited

U.S. PATENT DOCUMENTS

| | | | |
|---|---|---|---|
| 3,407,145 | 10/1968 | Brule | 350/354 X |
| 3,562,172 | 2/1971 | Ono et al. | 252/300 |
| 3,578,602 | 5/1971 | Ono et al. | 252/300 |
| 3,843,550 | 10/1974 | Hinnen | 252/586 |
| 3,980,480 | 9/1976 | Laridon | 430/345 X |
| 4,215,010 | 7/1980 | Hovey et al. | 252/586 |
| 4,289,497 | 9/1981 | Hovey | 350/354 X |
| 4,342,668 | 8/1982 | Hovey et al. | 252/586 |
| 4,440,672 | 4/1984 | Chu | 252/586 |

FOREIGN PATENT DOCUMENTS 48-23787  3/1973  Japan .
1227713  4/1971  United Kingdom .

OTHER PUBLICATIONS

Arnold, et al, *Tetrachedron*, 27, (1971), pp. 1699–1713, "Spektroskopische strukturuntersuchunger . . . ".

*Primary Examiner*—Teddy S. Gron
*Assistant Examiner*—Catherine S. Kilby
*Attorney, Agent, or Firm*—Irwin M. Stein

[57] ABSTRACT

Photochromic compounds represented by the graphic formula:

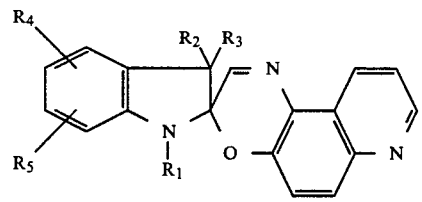

wherein:

(a) $R_1$ is selected from the group consisting of $C_1$–$C_8$ alkyl, phenyl, phen($C_1$–$C_4$) alkyl, allyl and mono- and di-substituted phenyl, said substituents being selected from $C_1$–$C_4$ alkyl and $C_1$–$C_5$ alkoxy;

(b) $R_2$ and $R_3$ are each selected from the group consisting of $C_1$–$C_5$ alkyl, phenyl, $C_1$–$C_4$ alkyl and $C_1$–$C_5$ alkoxy mono- and disubstituted phenyl, benzyl or combined to form a cyclic ring selected from the group consisting of an alicyclic ring containing from 6 to 8 carbon atoms (including the spiro carbon atom), norbornyl and adamantyl, and (c) $R_4$ and $R_5$ are each selected from the group consisting of hydrogen, $C_1$–$C_5$ alkyl, halogen, $C_1$–$C_5$ alkoxy, nitro, cyano and $C_1$–$C_8$ alkoxycarbonyl are described. Solvent systems which form photochromic compositions with the above compounds and articles containing the photochromic compound are described. The compound or compositions typically change from a colorless (nonexcited) or pale color, e.g., yellow, to blue after exposure to ultraviolet light.

25 Claims, No Drawings

PHOTOCHROMIC COMPOUND AND ARTICLES CONTAINING THE SAME

CROSS REFERENCE TO RELATED APPLICATIONS

This application is a continuation-in-part application of our abandoned application Ser. No. 548,600, filed Nov. 4, 1983 of the same title.

DESCRIPTION OF THE INVENTION

The present invention relates to novel photochromic compounds, and to compositions and articles containing such photochromic compounds. Photochromism is a reversible phenomenon illustrated by a compound which, when exposed to the radiation of light involving ultraviolet rays such as sunlight or the light of a mercury lamp, changes color and then returns to its original color if the radiation is discontinued or the compound is stored in the dark. A compound illustrating this property is called a "photochromic compound".

Various types of photochromic compounds have been synthesized and suggested for use in applications in which a color change or darkening is induced by sunlight. In particular, spiro(indoline) naphthoxazine compounds, as described in U.S. Pat. Nos. 3,562,172, 3,578,602, 4,215,010, and 4,342,668, show particular advantages for sunglasses and ophthalmic lenses. Such photochromic compounds either in crystalline form or in a solution or dispersion in a transparent medium change rapidly from a colorless state to blue when exposed to sunlight or ultraviolet radiation and return to the original colorless state by being allowed to stand in the dark or in the absence of strong ultraviolet radiation.

DETAILED DESCRIPTION OF THE INVENTION

In accordance with the present invention, there are provided novel photochromic compounds represented by the following graphic formula,

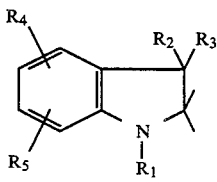

I

In the above graphic formula I, $R_1$ is selected from the group consisting of $C_1$–$C_8$ alkyl, phenyl, phen($C_1$–$C_4$)alkyl, allyl and mono- and disubstituted phenyl, said phenyl substituents being selected from $C_1$–$C_4$ alkyl and $C_1$–$C_5$ alkoxy. Preferably, $R_1$ is a $C_1$–$C_4$ alkyl, phenyl or benzyl radical.

$R_2$ and $R_3$ of formula I are each selected from the group consisting of $C_1$–$C_5$ alkyl, phenyl, mono- and disubstituted phenyl, benzyl or combine to form a cyclic ring selected from the group consisting of an alicyclic ring containing from 6 to 8 carbon atoms (including the spiro carbon atom), norbornyl and adamantyl. The phenyl substituents may be selected from $C_1$–$C_4$ alkyl and $C_1$–$C_5$ alkoxy radicals. Preferably, $R_2$ and $R_3$ are each selected from $C_1$–$C_5$ alkyl. When one of $R_2$ or $R_3$ is a tertiary alkyl radical, such as tertiary butyl or tertiary amyl, the other is preferably an alkyl radical other than a tertiary alkyl radical.

$R_4$ and $R_5$ in graphic formula I are each selected from the group consisting of hydrogen, $C_1$–$C_5$ alkyl, halogen, $C_1$–$C_5$ alkoxy, nitro, cyano and $C_1$–$C_8$ alkoxycarbonyl. $R_4$ and $R_5$ can be present on any two of the available carbon atoms of the indolino portion of the compound, i.e., on the 4, 5, 6, or 7 positions. Preferably, when the substituents are other than hydrogen, they are present at the 4 and 5, 5 and 6, 4 and 7 or 6 and 7 carbon atoms of the indolino moiety. While any halogen, i.e., chlorine, bromine, iodine and fluorine can be used, chlorine and bromine, especially chlorine is preferred. Preferably, $R_4$ and $R_5$ are selected from the group consisting of hydrogen, $C_1$–$C_2$ alkyl, chlorine, bromine, and $C_1$–$C_5$ alkoxy.

Of particular interest, are photochromic compounds represented by graphic formula I wherein $R_1$ is a $C_1$–$C_4$ alkyl, such as methyl, ethyl, n-propyl, isopropyl, n-butyl, secondary butyl, isobutyl and tertiary butyl; $R_2$ and $R_3$ are each methyl, ethyl or phenyl; and $R_4$ and $R_5$ are each hydrogen, methyl, methoxy, or chloro.

The photochromic compounds of the present invention can be dissolved in common organic solvents such as benzene, toluene, chloroform, ethylacetate, methylethylketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine, and ethylene glycol. The compounds can also be dispersed in liquids containing water, alcohols and other solvents.

The amount of solvent used to dissolve the photochromic compound should be sufficient to provide a photochromic composition which, when applied to a host material, will provide a photochromic amount of the compound in the host material.

The photochromic compounds of the present invention can also be dissolved in colorless or transparent solutions prepared from transparent polymers, copolymers or blends of such transparent polymers and a suitable organic solvent, e.g., polymers of transparent host materials described hereinafter dissolved in one or more of the aforesaid described organic solvents. Examples of such solutions include a polyvinylacetateacetone solution, a nitrocellulose-acetonitrile solution, a polyvinylchloride-methylethylketone solution, a polymethylmethacrylate-acetone solution, a cellulose acetate-dimethylformamide solution, a polyvinylpyrrolidone-acetonitrile solution, a polystyrene-benzene solution, and an ethyl cellulose-methylene chloride solution.

The aforesaid photochromic solutions or compositions can be applied to a transparent support, such as cellulose triacetate, polyethylene terephthalate or baryta paper and dried to obtain a photochromic material, which may be color formed by ultraviolet radiation to blue, and returned to colorless by removing the source of ultraviolet radiation.

The photochromic compounds of the present invention or compositions containing same can be applied to or incorporated within a solid transparent polymerized organic material, i.e., a synthetic plastic host material. Preferably, the host material is an optically clear material, e.g., materials suitable for ophthalmic elements, such as ophthalmic lenses or materials useful for applications such as windows, windshields, etc. A host material containing the photochromic compounds of the present invention can be used in the preparation of photochromic plastic films, sheets and lenses, such as lenses for sunglasses, ski goggles, visors, camera lenses and filters. As used herein, the term "optical element" is meant to include lenses and transparencies.

Examples of transparent host materials which can be used with the photochromic compounds of the present invention include: polymers of polyol(allyl carbonate) monomers, polyacrylates, poly(alkylacrylates) such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethyleneterephthalate, polystyrene, poly(styrene-methylmethacrylate) copolymers, poly(styrene-acrylonitrile) copolymer, and polyvinylbutyral. Transparent copolymers and blends of the transparent polymers are also suitable as host materials. Preferably, the host material is an optically clear polymerized organic material prepared from a polycarbonate, such as poly(4,4'-dioxydiphenol-2,2-propane), which is sold under the trademark, LEXAN; a polymethylmethacrylate, such as the material sold under the trademark, PLEXIGLAS; polymerizates of a polyol(allyl carbonate), especially diethylene glycol bis(allyl carbonate), which is sold under the trademark, CR-39, and its copolymers with for example vinyl acetate, e.g., copolymers of from 80–90 percent diethylene glycol bis(allyl carbonate) and 10–20 percent vinyl acetate; particularly 80–85 percent of the bis(allyl carbonate) and 15–20 percent vinyl, acetate cellulose acetate, cellulose propionate, cellulose butyrate, polystyrene and its copolymers with methyl methacrylate, vinyl acetate and acrylonitrile, and cellulose acetate butyrate.

Polyol (allyl carbonate) monomers which can be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., U.S. Pat. Nos. 2,370,567 and 2,403,113.

The polyol (allyl carbonate) monomers can be represented by the graphic formula:

$$R'\left(O-\overset{O}{\underset{\parallel}{C}}-O-R\right)_n$$

wherein R is the radical derived from an unsaturated alcohol and is commonly an allyl or substituted allyl group, R' is the radical derived from the polyol, and n is a whole number from 2–5, preferably 2. The allyl group (R) can be substituted at the 2 position with a halogen, most notably chlorine or bromine, or an alkyl group containing from 1 to 4 carbon atoms, generally a methyl or ethyl group. The R group can be represented by the graphic formula:

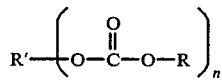

wherein $R_o$ is hydrogen, halogen, or a $C_1$–$C_4$ alkyl group. Specific examples of R include the groups: allyl, 2-chloroallyl, 2-bromoallyl, 2-fluoroallyl, 2-methallyl, 2-ethylallyl, 2-isopropylallyl, 2-n-propylallyl, and 2-n-butylallyl. Most commonly, R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$–$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

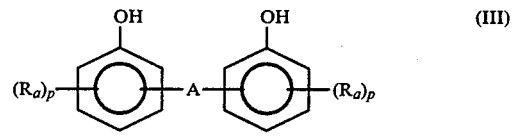

wherein A is a bivalent radical derived from an acyclic aliphatic hydrocarbon, e.g., an alkylene or alkylidene radical, having from 1 to 4 carbon atoms, e.g., methylene, ethylene, dimethylmethylene (isopropylidene), Ra represents lower alkyl substituents of from 1 to 3 carbon atoms, and p is 0, 1, 2, or 3. Preferably, the hydroxyl group is in the ortho or para position.

Specific examples of the radical R' include: alkylene groups containing from 2 to 10 carbon atoms such as ethylene, $(-CH_2-CH_2-)$ trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH_2-CH_2-$, and $-CH_2CH_2CH_2-O-CH_2CH_2CH_2-$; alkylene polyether groups such as $-CH_2CH_2-O-CH_2CH_2-O-CH_2CH_2-$ and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2CH_2-O-CH_2CH_2-O-CO-O-CH_2CH_2-O-CH_2CH_2-$; and isopropylidene bis(paraphenyl), i.e.,

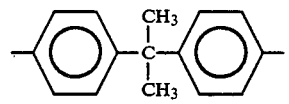

Most commonly, R' is $-CH_2CH_2-$, $-CH_2CH_2-O-CH_2CH_2-$, or $-CH_2CH_2-O-CH_2CH_2-O-CH_2CH_2-$.

Specific examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which can be utilized in the invention herein contemplated are:

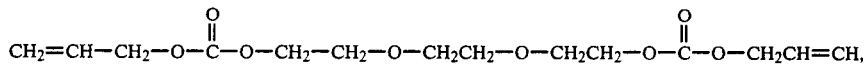

Triethylene Glycol bis(Allyl Carbonate)

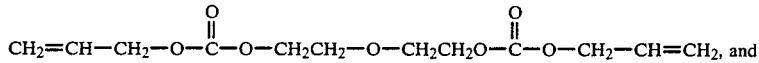

Diethylene Glycol bis(Allyl Carbonate)

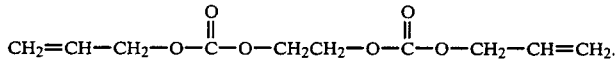

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

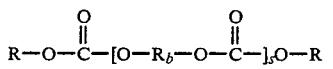

wherein R is as defined above $R_b$ is a bivalent radical, e.g., alkylene or phenylene, derived from a diol, and s is a whole number from 2 to 5. The related monomer species of diethylene glycol bis(allyl carbonate) can be represented by the graphic formula,

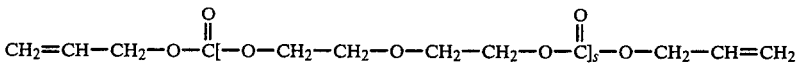

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4 etc.

In addition, a partially polymerized form of the polyol (allyl carbonate) monomer can be used. In that embodiment, the monomer is thickened by heating or partially polymerized by using small, e.g., 0.5–1.5 parts of initiator per hundred parts of monomer (phm) to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

The amount of the photochromic compound or composition-containing same applied to or incorporated into the host material is not critical and depends generally upon the intensity of the color of the composition desired upon irradiation thereof and upon the method used to incorporate or apply the photochromic compound. Typically, the more compound added, the greater the color intensity. Generally such amount can be described as a photochromic amount. Usually, the amount of photochromic compound incorporated into the host material ranges from about 0.01 to about 20 percent by weight, more usually from about 0.05 to about 10 percent by weight, based on the weight of the host material. Stated another way, the amount of photochromic compound used to impart a photochromic effect will typically vary from about 1 to about 10 milligrams of the photochromic compound per square inch of the surface of the host material independent of the thickness of the host material article. Hence, the photochromic compound is present in a higher concentration in thin samples, films, or coatings, and in a lower concentration in thick samples.

Solutions of the photochromic compounds of the present invention in ethanol are typically colorless or pale yellow, green or blue. These solutions undergo a rapid change in color to purple or blue upon exposure to ultraviolet radiation and return to their original color or colorless state upon removal of the source of ultraviolet radiation. Such color change may be repeated numerous times.

The photochromic compounds or compositions of the present invention can be applied to or incorporated into a host material by methods known in the art. Such methods include dissolving or dispersing the compound in the host material, i.e., imbibation of the photochromic compound by immersion, thermal transfer, or coating, and incorporation of the photochromic compound as a separate layer between adjacent layers of the host material. The term "imbibation" or "imbibe" is intended to mean and include diffusion of the photochromic compound alone into the host material, solvent assisted diffusion, absorption of the photochromic compound into a porous polymer, vapor phase transfer, and other such transfer mechanisms. For example:

(a) The photochromic compounds or compositions of the present invention can be mixed with a polymerizable composition that, upon curing, produces an optically clear polymeric host material and the polymerizable composition cast as a film, sheet or lens, or injection molded or otherwise formed into a sheet or lens;

(b) The photochromic compounds of the present invention can be dissolved or dispersed in water, alcohol or other solvents or solvent mixtures and then imbibed into the solid host material by immersion for from several minutes to several hours, e.g., 2–3 minutes to 2–3 hours of the host material in a bath of such solution or dispersion. The bath is conventionally at an elevated temperature, usually in the range of 50°–120° C. Thereafter, the host material is removed from the bath and dried;

(c) The photochromic compounds and compositions may also be applied to the surface of the host material by any convenient manner, such as spraying, brushing, spin-coating or dip-coating from a solution or dispersion of the photochromic material in the presence of a polymeric binder. Thereafter, the photochromic compound is imbibed by the host material by heating it, e.g, in an oven, for from a minute to several hours at temperatures in the range of from 80°–180° C.;

(d) In a variation of the above imbibation procedure, the photochromic compound or composition can be deposited onto a temporary support, e.g., a sheet of craft paper, aluminum foil, polymer film or fabric, which is then placed in contact with the host material and heated, e.g., in an oven;

(e) The photochromic compounds can be dissolved or dispersed in a transparent polymeric material which can be applied to the surface of the host in the form of an adherent film by any suitable technique such as spraying, brushing, spin-coating or dip-coating; and (f) Finally, the photochromic compounds can be incorporated or applied to a transparent polymeric material by any of the above-mentioned methods, which can then be placed within the host material as a discrete layer intermediate to adjacent layers of the host material.

The photochromic compounds of the present invention can be synthesized by reaction of the corresponding nitroso-hydroxy quinoline compound with the corresponding indolines (Fischer's base) or indolium salt, e.g., the iodide salt, compound. The two precursor materials are refluxed in a suitable solvent, such as toluene or isopropanol, containing a base, such as triethylamine, until the reaction is completed. The photochromic compound is recovered from the reaction mixture, e.g., by filtration, and recrystallized, if necessary, to obtain a more purified product.

The present process is more particularly described in the following examples which are intended as illustrative only since numerous modifications and variations therein will be apparent to those skilled in the art.

EXAMPLE 1

(Method A)

A suspension of 5-nitroso-6-quinolinol (1.74 grams, 0.01 mole) in 70 milliliters (ml) of toluene was heated to 100°–108° C. with stirring. To this heated suspension was slowly added over 15 minutes 3.43 grams of 1,2,3,5,6-pentamethyl-3-ethylindolium iodide (0.01 mole) suspended in 40 ml of toluene containing 2.01 grams of triethylamine (0.02 mole) and 0.5 ml of ethanol. The flask containing the indolium iodide was washed with 30 ml of toluene and the toluene wash liquor added to the reaction vessel. The mixture in the reaction vessel was refluxed for four hours and thereafter the reaction mixture was decanted and allowed to evaporate to almost dryness. A mixture of dark green gum and a small amount of crystalline material resulted. The almost dried mixture was soaked with 7–8 ml of fresh toluene, filtered and washed with 4 ml of toluene twice. The filtrate and washings were combined and allowed to evaporate. A crystalline material slowly formed in the gum over 5 days. The thick gum was soaked with 2–3 ml of ethanol, filtered, washed with ethanol and air dried. A yellowish-green powder (0.81 grams) was obtained. The filtrate and washings were combined and allowed to evaporate, thereby obtaining an additional 0.2 grams of the green crystalline material which was combined with the first crop of crystals.

The combined crude product was recrystallized from an acetone: n-hexane mixture (2:3 V/V). A yellowish-green microcrystalline powder weighing about 0.76 grams was obtained. The material was identified as 1,3,5,6-tetramethyl-3-ethylspiro[indoline-2,3'[3H] pyrido [3,2 f] [1,4]-benzoxazine] by Nuclear Magnetic Resonance (NMR) spectroscopy and elemental analysis. Elemental analysis of a sample of the product prepared from the same reactants but in another preparation was found to be 77.45 wt. % carbon, 6.88 wt. % hydrogen and 11.11 wt. % nitrogen. These values substantially agree with the theoretical values of 77.60 wt. % carbon, 6.78 wt. % hydrogen, and 11.31 wt. % nitrogen.

(Method B)

A suspension of 5-nitroso-6-quinolinol (0.73 grams, 0.0042 mole) in 30 ml of isopropanol was heated to reflux temperature. To this suspension was slowly added over 15 minutes 1.44 grams (0.0042 mole) of 1,2,3,5,6-pentamethyl-3-ethylindolium iodide dissolved in 35 ml of isopropanol containing 0.85 grams (0.0085 mole) of triethylamine. The resulting blue reaction mixture was refluxed for two hours and then allowed to cool to room temperature. The blue solution was allowed to evaporate overnight and crystals formed in the almost dry solution. The crystals were filtered, washed with about 2 ml of isopropanol and then air dried. A dark olive green powder (1.32 grams) was obtained. This powder was added to 120 ml of boiling n-hexane and insoluble powder removed by filtration. Active charcoal (1.5 grams) was added to the filtrate and the mixture stirred for a few minutes and then filtered. The charcoal-free filtrate was reduced in volume to about 40 ml and stored overnight in a refrigerator. Yellow crystals were found to have formed. After decantation, the yellow crystals were washed with fresh n-hexane and then air dried. The dried crystals (0.46 grams) were identified by NMR as 1,3,5,6-tetramethyl-3-ethylspiro [indoline-2,3'[3H] pyrido [3,2-f] [1,4]-benzoxazine].

EXAMPLES 2–9

Other photochromic compounds within the scope of graphic formula I were prepared by reaction of 5-nitroso-6-quinolinol with other indoline or indolium iodide compounds having the substituents identified in Table I using toluene as the reaction solvent. When the indolium iodide was used, triethylamine was also used, as described in Example 1. The products of the reaction were purified by various conventional purification techniques as exemplified by Example 1 and other examples illustrating the preparation of the photochromic compounds of the present invention.

TABLE I

| Example No. | Substituent | | | | | Description |
|---|---|---|---|---|---|---|
| | $R_1$ | $R_2$ | $R_3$ | $R_4$ | $R_5$ | |
| 2 | $CH_3$ | $CH_3$ | $CH_3$ | H | H | Beige-Green |

TABLE I-continued

| Example No. | R₁ | R₂ | R₃ | R₄ | R₅ | Description |
|---|---|---|---|---|---|---|
| 3 | CH₃ | CH₃ | CH₃ | 5-CH₃ | 6-CH₃ | Powder Yellow-Green Powder |
| 4 | CH₃ | CH₃ | CH₃ | 5-CH₃O | H | Yellow Powder |
| 5 | CH₃ | CH₃ | CH₃ | 7-CH₃ | 6-Cl | Yellow Powder |
| 6 | CH₃ | CH₃ | C₂H₅ | H | H | Dark Green Paste |
| 7 | CH₃ | CH₃ | phenyl | H | H | Dark Green Powder |
| 8 | CH₃ | phenyl | phenyl | H | H | Yellow-Green Powder |
| 9 | CH₃ | spiro(pentamethylene) | | H | H | Pale Yellow Solid |

Ethanol solutions of each of the compounds of Examples 1–9 changed to blue when irradiated with ultraviolet light at room temperature. The solutions returned to their original hue or colorless condition after the UV light was removed.

EXAMPLE 10

A suspension of 5-nitroso-6-quinolinol (1.05 grams, 0.006 mole) in 30 milliliters (ml) of toluene was heated to reflux with stirring. To this heated suspension was slowly added over 20 minutes 1.37 grams of 1-butyl-3-methyl-3-ethyl-2-methylene indoline (0.006 mole) dissolved in 20 ml of toluene. The mixture in the reaction vessel was refluxed for three hours and thereafter the reaction mixture was transferred to an evaporating dish and allowed to evaporate to almost dryness. The almost dried mixture was soaked with 7 ml of fresh toluene, filtered and washed with 3 ml of toluene twice. The filtrate and washings were combined and allowed to evaporate. A viscous dark blue gum formed. The resulting gum-paste was redissolved in about 20 ml of diethyl ether, filtered and the filtrate allowed to evaporate in a hood. When one drop of the ether solution was diluted with ethanol and irradiated with ultraviolet light at room temperature for about 30 seconds, the solution turned a blue color. The blue color disappeared in about 5 minutes when the ultraviolet light was removed.

The gum paste obtained from evaporating the ether solution was dried in a vacuum desiccator for several days. The dried paste was dissolved in 10 ml of toluene and dehydrated with 5.6 grams of sodium sulfate, filtered, and washed with 3 ml of toluene. The filtrate and washing were combined and evaporated in a hood-yielding a dark blue paste.

EXAMPLE 11

One part of the photochromic compounds of Examples 1–10 were each incorporated into a sprayable lacquer solution of 10 parts of a commercial lacquer (3M Company-lacquer No. 2253), 10 parts toluene and 10 parts methyl ethyl ketone. The lacquer solution was sprayed onto the surface of a 1 inch (2.54 cm) by 1 inch (2.54 cm) by 2 mm thick coupon of a polymer prepared from diethylene glycol bis (allyl carbonate). After drying, the coated coupon was heated in an air oven at 160° C. for 20 minutes. After cooling, the residual lacquer was stripped off with adhesive tape and the surface cleaned with an acetone-wetted cloth. The photochromic tablet was tested for photochromic response to activation by artificial sunlight. Results are tabulated in Table II.

TABLE II

| Example No. | $\Delta T_R$, % | $\Delta OD$, $\lambda$max | $t_{\frac{1}{2}}$, sec. |
|---|---|---|---|
| 1 | 76 | 1.33 | 57 |
| 2 | 48 | 0.41 | 14 |
| 3 | 72 | 1.13 | 41 |
| 4 | 66 | 0.98 | 45 |
| 5 | — | 0.16 | 8 |
| 6 | — | 0.49 | 18 |
| 7 | — | 0.61 | 21 |
| 8 | 37 | 0.29 | 21 |
| 9 | 46 | 0.40 | 26 |
| 10 | 59 | 0.67 | 21 |

1. $\Delta T_R$ - The percent reduction in visible light transmission (measured using a photopic filter) induced after 4 minutes irradiation with artificial sunlight.
2. $\Delta OD$ - The change in saturation optical density measured in the range of 580–620 nm induced by irradiation for 4 minutes with artificial sunlight.
3. $t_{\frac{1}{2}}$ - The half-life in seconds for the transmission of a sample to increase by 21% from 42% transmission (based on transmission in the clear state) after irradiation with artificial sunlight.

EXAMPLE 12

Photochromic compounds of the prior art were applied to a coupon made from diethylene glycol (bis)allyl carbonate) in the same manner as described in Example 11. The photochromic response to these articles is compared to that of Examples 2, 3, and 4 in Table III. These photochromic compounds can be depicted by the following graphic formula,

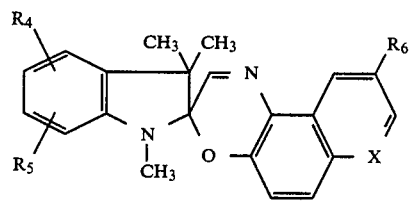

wherein R₄, R₅, R₆ and X are identified in Table III.

TABLE III

| | | Prior Art U.S. Pat. No 3,562,172 X = C, R₆ = H | | Prior Art U.S. Pat. No. 4,215,010 X = C, R₆ = CH₃O | | Examples 2, 3, 4 X = N, R₆ = H | |
|---|---|---|---|---|---|---|---|
| R₄ | R₅ | ΔTR, % | ΔOD at max | ΔTR % | ΔOD at max | TR, % | ΔOD at max |
| H | H | 40 | 0.34 | 29 | 0.23 | 48 | 0.41 |
| H | CH₃O | 34 | 0.31 | 53 | 0.46 | 66 | 0.98 |
| CH₃ | CH₃ | 34 | 0.31 | 57 | 0.65 | 72 | 1.13 |

EXAMPLE 13

A suspension of 5-nitroso-6-quinolinol (0.52 grams, 0.003 mole) in 20 milliliters (ml) of toluene was heated to about 100° C. with stirring. To this heated suspension was slowly added over about 20 minutes 1.75 grams of 1,2-dimethyl-3,3-bis(p-methoxyphenyl) indolium iodide (0.003 mole) suspended in 20 ml of toluene containing 0.60 grams of triethylamine (0.006 mole). The mixture in the reaction vessel was maintained at about 100° C. for 2.5 hours and the degree of reaction monitored by thin layer chromotography (TLC). The reaction was almost complete after 1 hour. After 2.5 hours at about 100° C., an additional 0.17 grams (0.001 mole) of 5-nitroso-6-quinolinol was added to the reaction vessel, but total reaction of the indolium iodide reactant was not obtained even after 2 hours at about 100° C. The solids in the reaction mixture were separated by decantation and the remaining liquid allowed to evaporate to almost dryness. Olive green crystals formed in the almost dried paste. The almost dried product was soaked with 7 ml of fresh toluene, filtered and slowly washed with 3 ml of toluene. A large amount of the crystalline powder product did not dissolve in the toluene. The crystalline insoluble powder was washed with ethanol and air dried. An olive green powder (0.79 grams) was obtained. A sample of the powder was dissolved in ethanol and irradiated with ultraviolet light (366 nm) for about 30 seconds. The solution turned from pale green to blue and returned to pale green when the ultraviolet light was removed.

EXAMPLE 14

A suspension of 5-nitroso-6-quinolinol (1.39 grams, 0.008 mole) in 35 ml of toluene was heated to about 100° C. with stirring. To this heated suspension was slowly added over 20–30 minutes 2.95 grams of 1,2,5,6,-tetramethyl-3,3-spiro (cyclohexyl)-[3H] indolium iodide suspended in 35 ml of toluene containing 1.6 grams of triethylamine (0.016 mole). The progress of the reaction was checked by TLC. The mixture in the reaction vessel was maintained at about 100° C. for three hours. Thereafter, the reaction mixture (a dark brown solution) was allowed to evaporate to almost dryness. The resulting paste was soaked with 6 ml of fresh toluene for several minutes, filtered to remove insoluble material and the resulting solids washed with 2 ml of toluene. The filtrate and washing were combined and allowed to evaporate. A dark brown paste (2.07 grams) resulted. A small amount (about 1 milligram) of the paste was dissolved in about 2–3 ml of ethanol and the resulting solution exposed to ultraviolet light (366 nm) at room temperature. The solution turned pale blue and returned to its original hue in about 2 minutes after the ultraviolet light source was removed.

EXAMPLE 15

In accordance with the procedure of Example 14, 1.22 grams (0.007 mole) of 5-nitroso-6-quinolinol was reacted with 1.70 grams (0.007 mole) of 1-allyl-3,5,6-trimethyl-3-ethyl-2-methylene indoline in 60 ml of toluene at about 100° C. for about three hours. The reaction mixture was evaporated to almost dryness and the resulting paste soaked with 6 ml of toluene for several minutes and then filtered. The insoluble material was washed with 2 ml of toluene. The filtrate and washing were combined and allowed to evaporate. A dark (greenish) brown paste (2.49 grams) was obtained. A small amount of the paste was dissolved in 2–3 ml of ethanol and the resulting pale yellow solution exposed to ultraviolet light (366 nm). The solution turned green and returned to its original hue in about 1–2 minutes after the ultraviolet light source was removed.

EXAMPLE 16

In accordance with the procedure of Example 14, a suspension of 1.74 grams (0.01 mole) of 5-nitroso-6-quinolinol in 40 ml of toluene was reacted with 3.57 grams (0.01 mole) of 1,3-diethyl-2,3,5,6-tetramethyl indolium iodide in 40 ml of toluene containing 2 grams (0.02 mole) of triethylamine. After three hours of reaction, a dark blue-green solution was obtained and this solution allowed to evaporate to almost dryness. The resulting paste was soaked with 6 ml of toluene for several minutes and filtered. The resulting solid was washed with 2 ml of toluene and combined with the filtrate. The resulting dark solution was allowed to evaporate to form 3.28 grams of a dark green paste. A small amount of the paste was tested for photochromicity in accordance with the procedure of Example 14. The ethanol solution of the paste was a pale green which became deep blue upon exposure to ultraviolet light. The solution returned to pale green in about 3–4 minutes after removal of the ultraviolet light.

EXAMPLE 17

In accordance with the procedure of Example 14, 1.74 grams (0.01 mole) of 5-nitroso-6-quinolinol and 2.57 grams of 1-butyl-3-ethyl-3,5,6-trimethyl-2-methylene indoline were refluxed in 70 ml of toluene for 3 hours. The resultant product was a dark blue paste. An ethanol solution of a small amount of the paste was a pale to medium blue which became sky blue upon exposure to ultraviolet light. The solution returned to its original hue in about 5 minutes after removal of the ultraviolet light.

EXAMPLE 18

In accordance with the procedure of Example 14, 1.22 grams of 5-nitroso-6-quinolinol was suspended in 50 ml of hot toluene. To this suspension was added slowly over about 10 minutes 1.70 grams of 1-butyl-3,3,5,6-tetramethyl-2-methylene indoline diluted in 20 ml of toluene. The resulting mixture was refluxed for 3 hours. An ethanol solution of the resultant product turned a dark blue upon exposure to ultraviolet light and returned to its original hue in about 4–5 minutes after the light was removed.

The above procedure was repeated using isopropanol as the solvent. The product was a very dark green paste.

EXAMPLE 19

The procedure of Example 18 was followed except that 2.04 grams (0.007 mole) of the Fischer's base, 1-benzyl-3,5,6-trimethyl-3-ethyl-2-methylene indoline, was used. An ethanol solution of the resultant product was pale green. The solution turned medium blue upon exposure to ultraviolet light and returned to its original hue in about 3–4 minutes after the light was removed.

EXAMPLE 20

To a suspension of 0.89 grams of 5-nitroso-6-quinolinol (0.005 mole) in boiling isopropanol was slowly added 1.32 grams (0.005 mole) of 1,3,5,6-tetramethyl-3-phenyl-2-methylene indoline dissolved in 25 ml of isopropanol. The reaction mixture was refluxed for one hour. The resulting dark blue reaction solution was evaporated overnight and a dark blue (almost black) gum was formed. Further evaporation resulted in the formation of a hard cake with significant decomposition. Photochromicity of the product was confirmed in silica gel matrix after the gum had been chromatographed on a thin layer chromatograph plate.

A summary of the compounds of Examples 17–20 is found in Table IV.

TABLE IV

| Example No. | $R_1$ | $R_2$ | $R_3$ | $R_4$ | $R_5$ | Description |
|---|---|---|---|---|---|---|
| 17 | n-$C_4H_9$ | $C_2H_5$ | $CH_3$ | $CH_3$ | $CH_3$ | Dark Blue Paste |
| 18 | n-$C_4H_9$ | $CH_3$ | $CH_3$ | $CH_3$ | $CH_3$ | Dark Green Paste |
| 19 | benzyl | $C_2H_5$ | $CH_3$ | $CH_3$ | $CH_3$ | Dark Green Paste |

TABLE IV-continued

| Example No. | R₁ | R₂ | R₃ | R₄ | R₅ | Description |
|---|---|---|---|---|---|---|
| 20 | CH₃ | phenyl | CH₃ | CH₃ | CH₃ | Dark Blue Gum |

Although the present invention has been described with reference to specific details of certain embodiments thereof, it is not intended that such details should be regarded as limitations upon the scope of the invention except as and to the extent that they are included in the accompanying claims.

We claim:

1. A photochromic compound represented by the following graphic formula:

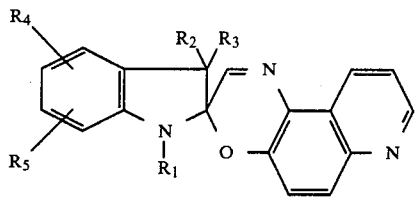

wherein:
(a) R₁ is selected from the group consisting of C₁-C₈ alkyl, phenyl, phen(C₁-C₄)alkyl, allyl and mono- and disubstituted phenyl, said phenyl substituents being selected from C₁-C₄ alkyl and C₁-C₅ alkoxy;
(b) R₂ and R₃ are each selected from the group consisting of C₁-C₅ alkyl, phenyl, C₁-C₄ alkyl and C₁-C₅ alkoxy mono- and disubstituted phenyl, benzyl or combine to form a cyclic ring selected from the group consisting of an alicyclic ring containing from 6 to 8 carbon atoms (including the spiro carbon atoms), norbornyl and adamantyl, and
(c) R₄ and R₅ are each selected from the group consisting of hydrogen, C₁-C₅ alkyl, halogen, C₁-C₅ alkoxy, nitro, cyano and C₁-C₈ alkoxycarbonyl.

2. A photochromic compound of claim 1 wherein:
(a) R₁ is selected from the group consisting of C₁-C₄ alkyl, phenyl and benzyl,
(b) R₂ and R₃ are each selected from C₁-C₅ alkyl,
(c) and R₄ and R₅ are each selected from the group consisting of hydrogen, C₁-C₂ alkyl, chlorine, bromine, and C₁-C₅ alkoxy.

3. A photochromic compound of claim 1 wherein R₁, R₂ and R₃ are methyl and R₄ and R₅ are hydrogen.

4. A photochromic compound of claim 1 wherein R₁, R₂, and R₃ are methyl, R₄ is methoxy, and R₅ is hydrogen.

5. A photochromic compound of claim 1 wherein R₁, R₂, R₃ and R₄ are methyl and R₅ is chloro.

6. The compound 1,3,5,6-tetramethyl-3-ethylspiro [indoline-2,3'[3H] pyrido[3,2-f] [1,4] benzoxazine].

7. The compound 1,3,3,5,6-pentamethylspiro [indoline-2,3'[3H] pyrido[3,2-f][1,4] benzoxazine].

8. The compound 1,3,4,5-tetramethyl-3-ethylspiro [indoline-2,3'[3H] pyrido [3,2-f][1,4]benzoxazine].

9. The compound 1,3,3,4,5-pentamethylspiro[indoline-2,3'[3H] pyrido[3,2-f][1,4]benzoxazine].

10. A photochromic compound of claim 1 wherein R₁, R₂, R₃, R₄ and R₅ are methyl.

11. A photochromic compound of claim 1 whereub R₁, R₂, R₄ and R₅ are methyl and R₃ is ethyl.

12. A photochromic article comprising a solid transparent polymerized organic host material containing a photochromic amount of a photochromic compound represented by the graphic formula:

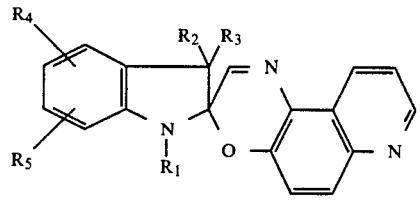

wherein:
(a) R₁ is selected from the group consisting of C₁-C₈ alkyl, phenyl, phen(C₁-C₄)alkyl, allyl and mono- and disubstituted phenyl, said phenyl substituents being selected from C₁-C₄ alkyl and C₁-C₅ alkoxy;
(b) R₂ and R₃ are each selected from the group consisting of C₁-C₅ alkyl, phenyl, C₁-C₄ alkyl and C₁-C₅ alkoxy mono- and disubstituted phenyl, benzyl or combine to form a cyclic ring selected from the group consisting of an alicyclic ring containing from 6 to 8 carbon atoms (including the spiro carbon atom), norbornyl and adamantyl, and
(c) R₄ and R₅ are each selected from the group consisting of hydrogen, C₁-C₅ alkyl, halogen, C₁-C₅ alkoxy, nitro, cyano and C₁-C₈ alkoxycarbonyl.

13. The photochromic article of claim 12 wherein the transparent host material is selected from the group consisting essentially of polymers of polyol(allyl carbonate), copolymers of polyol(allyl carbonate) and vinyl acetate, polyacrylates, poly(alkylacrylates), cellulose acetate, cellulose triacetate, cellulose acetate propionate, cellulose acetate butyrate, poly(vinyl acetate), poly(vinyl alcohol), polycarbonate, polystyrene, poly(styrene-methylmethacrylate)copolymers, poly(styrene-acrylonitrile)copolymers, and polyvinyl butyral.

14. The photochromic article of claim 13 wherein the transparent host material is selected from poly[diethylene glycol bis(allyl carbonate)] and its copolymers with vinyl acetate.

15. The photochromic article of claim 13 wherein the photochromic compound is represented by the graphic formula:

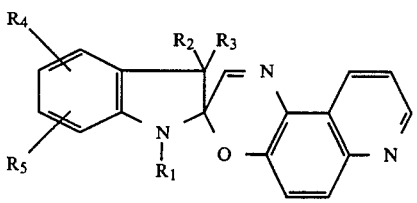

wherein:
(a) R₁ is selected from the group consisting of C₁-C₄ alkyl, allyl, phenyl and benzyl,
(b) R₂ and R₃ are each selected from C₁-C₅ alkyl,
(c) and R₄ and R₅ are each selected from the group consisting of hydrogen, C₁-C₂ alkyl, chlorine, bromine, and C₁-C₅ alkoxy.

16. A photochromic article comprising a solid transparent polymerized organic host material selected from the group consisting of polycarbonate, polymers of polyol (allyl carbonate), copolymers of polyol(allyl carbonate) and vinyl acetate, polymethylmethacrylate, cellulose acetate, cellulose propionate, cellulose butyrate, cellulose acetate butyrate, polystryrene, poly(styrene-methylmethacrylate)copolymer, and poly(styrene-acrylonitrile)copolymer, containing a photochromic amount of a photochromic compound represented by the graphic formula:

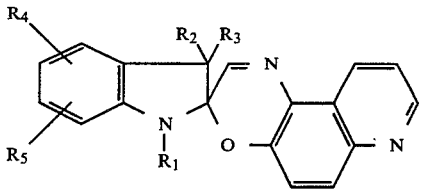

wherein:
(a) $R_1$ is selected from the group consisting of $C_1$–$C_4$ alkyl, phenyl and benzyl,
(b) $R_2$ and $R_3$ are each selected from $C_1$–$C_5$ alkyl,
(c) and $R_4$ and $R_5$ are each selected from the group consisting of hydrogen, $C_1$–$C_2$ alkyl, chlorine, bromine, and $C_1$–$C_5$ alkoxy.

17. The photochromic article of claim 16 wherein the photochromic compound is present in amounts of from 0.05 to 10 weight percent.

18. The photochromic article of claim 17 wherein the host material is selected from poly[diethylene glycol bis(allyl carbonate)] and its copolymers with vinyl acetate.

19. The photochromic article of claim 18 wherein the photochromic compound is one wherein $R_1$, $R_2$, $R_4$ and $R_5$ are methyl and $R_3$ is selected from methyl and ethyl.

20. The photochromic article of claim 18 wherein the copolymer is from 80–90 percent diethylene glycol bis(allyl carbonate) and 10–20 percent vinyl acetate.

21. An optical photochromic element comprising a host material selected from homopolymers of a polyol(allyl carbonate) and copolymers of polyol(allyl carbonate) and vinyl acetate and a photochromic amount of a photochromic compound represented by the graphic formula:

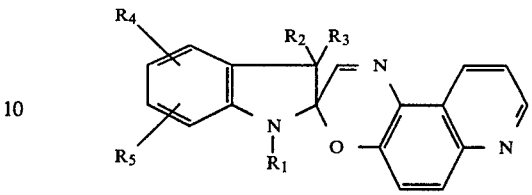

wherein:
(a) $R_1$ is selected from the group consisting of $C_1$–$C_4$ alkyl, phenyl and benzyl,
(b) $R_2$ and $R_3$ are each selected from $C_1$–$C_5$ alkyl,
(c) and $R_4$ and $R_5$ are each selected from the group consisting of hydrogen, $C_1$–$C_2$ alkyl, chlorine, bromine, and $C_1$–$C_5$ alkoxy.

22. The optical element of claim 21 wherein the polyol(allyl carbonate) is diethylene glycol bis(allyl carbonate), the copolymer is 80–90 percent diethylene glycol bis(allyl carbonate) and 10–20 percent vinyl acetate and the amount of photochromic compound is from 0.05 to 10 weight percent.

23. The optical element of claim 21 wherein the photochromic compound is one wherein $R_1$, $R_2$, $R_4$ and $R_5$ are methyl and $R_3$ is selected from methyl and ethyl.

24. The optical element of claim 23 wherein the element is a lens.

25. The optical lens of claim 24 wherein the photochromic compound is dispersed across at least one surface of the lens.

* * * * *